United States Patent [19]
Crowley et al.

[11] Patent Number: 5,658,876
[45] Date of Patent: Aug. 19, 1997

[54] ACTIVIN ANTAGONISTS AS NOVEL CONTRACEPTIVES

[75] Inventors: William F. Crowley, Newtonville, Mass.; J. Larry Jameson, Winnetka, Ill.; Alan L. Schneyer, Arlington, Mass.; Jeffrey Weiss, Chicago, Ill.

[73] Assignee: The General Hospital Corporation, Boston, Mass.

[21] Appl. No.: 234,261

[22] Filed: Apr. 28, 1994

[51] Int. Cl.$^6$ .......................... A61K 38/03; A61K 38/16; A61K 38/17
[52] U.S. Cl. .................... 514/2; 514/12; 514/21; 514/841; 514/843
[58] Field of Search .................... 514/8, 12, 13, 514/14, 15, 16, 21, 841, 843, 2, 17, 18, 19, 20; 530/397, 398, 399

[56] References Cited

U.S. PATENT DOCUMENTS

| | | | |
|---|---|---|---|
| 4,010,256 | 3/1977 | Parlow | 424/88 |
| 4,552,864 | 11/1985 | Antoni et al. | 514/15 |
| 4,740,587 | 4/1988 | Ling et al. | 530/324 |
| 4,798,885 | 1/1989 | Mason et al. | 530/350 |
| 4,864,019 | 9/1989 | Vale et al. | 530/387 |
| 5,041,538 | 8/1991 | Ling et al. | 530/395 |
| 5,196,192 | 3/1993 | De Kretser et al. | 514/8 |
| 5,216,126 | 6/1993 | Cox et al. | 530/350 |

FOREIGN PATENT DOCUMENTS

| | | |
|---|---|---|
| WO82/04250 | 12/1982 | WIPO. |
| WO91/10444 | 7/1991 | WIPO. |
| 06456 | 3/1994 | WIPO. |

OTHER PUBLICATIONS

Alexander et al. "The Effects of Activin on Follicle-Stimulating Hormone Secretion and Biosynthesis in Human Glycoprotein Hormone-Producing Pituitary Adenomas" J. Clin. Endocrin. & Metab. 72:1261–1267 (1991).

Attardi et al. "Rapid Stimulatory Effect of Activin-A on Messenger RNA Encoding the Follicle-Stimulating Hormone β-Subunit in Rat Pituitary Cell Cultures" Molec. Endocrin. 4:721–726 (1990).
Kogawa et al. "Activin-Binding Protein is Present in Pituitary" Endocrinology 128:1434–1440 (1991).
Sugino et al. "Molecular Multiplicity of Activin-Binding Protein/Follistatin from Porcine Ovary" The Endocrine Society Abstracts, p. 408, No. 1510 (1991).
Xiao et al. "Studies on the Mechanism of Activin and FSH Suppressing Protein in Cultured Rat Granulosa Cells" The Endocrie Society Abstracts, p. 370, No. 1359 (1991).
Campen et al., "Characterization of Activin A Binding Sites on the Human Leukemia Cell Line K562" Biochem. & Biophys. Res. Comm., 157:844–849 (1988).
Centrella et al., "Activin-A Binding and Biochemical Effects in Osteoblast-Enriched Cultures from Fetal-Rat Parietal Bone" Molec. & Cellular Bio., 11:250–258 (1991).
Hemmati-Brivanlou et al., "A truncated activin receptor inhibits mesoderm induction and formation of axial structures in Xenopus embryos" Nature, 359:609–614 (1992).
Mason et al., "Complementary DNA sequences of ovarian follicular fluid inhibin show precursor structure and homology with transforming growth factor-β" Nature, 318:659–663 (1985).
Mason et al. "Structure of Two Human Ovarian Inhibins" Biochem. & Biophys. Comm., 135:957–964 (1986).
Corrigan et al., "Evidence for an Autocrine Role of Activin B within Rat Anterior Pituitary Cultures" Endocrinology, 128:1682–1684 (1991).

(List continued on next page.)

Primary Examiner—Jeffrey E. Russel
Attorney, Agent, or Firm—Fish & Richardson P.C.

[57] ABSTRACT

A method for contraception which features administering to a patient a contraceptive agent having activin-antagonist activity. The contraceptive agent results in inhibition of the activin-stimulated release of FSH, thereby resulting in a decrease in fertility and facilitating contraception in the patient.

3 Claims, 9 Drawing Sheets

OTHER PUBLICATIONS

Weiss et al., "Dynamic Regulation of Follicle–Stimulating Hormone–β Messenger Ribonucleic Acid Levels by Activin and Gonadotropin–Releasing Hormone in Perifused Rat . . . " Endocrinology, 131:1403–1408 (1992).

Weiss et al., "Perifusion of Rat Pituitary Cells with Gonadotropin–Releasing Hormone, Activin, and Inhibin Reveals Distinct Effects on Gonadotropin Gene Expression and Secretion" Endocrinology, 132:2307–2311 (1993).

ACTIVIN ANTAGONISTS AS NOVEL CONTRACEPTIVES

The invention described in this application was supported by the National Center for Infertility, research grants HD29164 and HD28138. The U.S. government has certain rights in this invention.

This invention relates to contraception.

BACKGROUND OF THE INVENTION

Release of FSH from the anterior pituitary is essential for gametogenesis, as FSH results in stimulation of spermatogenesis in the testis, as well as maturation of the oocyte and secretion of estradiol by the ovarian follicles. The biosynthesis and secretion of FSH within the anterior pituitary is controlled through the complex interaction of several hormones. These include hypothalamic gonadotropin-releasing hormone (GnRH), gonadal steroids, and the recently-identified gonadal peptides, inhibin, activin, and follistatin.

Inhibin and follistatin have the ability to inhibit the synthesis and secretion of FSH by the pituitary (De Jong et al., *Nature* 263: 71–72 (1976)), while activin has been shown to be capable of stimulating FSH synthesis and release (Vale et al., *Nature* 321: 776–779 (1986); Ling et al., *Nature* 321: 779–782 (1986)). Inhibin is a heterodimeric glycoprotein composed of an $\alpha$ subunit linked to one of two $\beta$ subunits ($\beta_A$ or $\beta_B$), whereas activin consists of heterodimers or homodimers of inhibin $\beta$ subunits. Although originally isolated from the gonads, both inhibin and activin have been detected in the pituitary where they play an autocrine/paracrine role in the control of FSH gene expression (Meunier et al., *Proceedings of the National Academy of Sciences* 85:247–251, (1988)). In addition, recent immunohistochemical studies have determined that inhibin/activin subunit proteins localized in the pituitary gonadotropes are responsible for FSH and LH synthesis (Roberts et al., 1989, *Endocrinology* 124:552–554).

Both activin and inhibin subunits have been isolated from natural sources. In Mason et al., U.S. Pat. No. 4,798,885, the amino acid sequences of the $\alpha$, $\beta_A$ and $\beta_B$ subunits of human and porcine inhibin are described and are used to identify the amino acid sequences of activin. Mason et al. discuss the use of activin as a fertility-inducing therapeutic capable of stimulating FSH release.

The use of activin to increase fertility in a male mammal is described in Attie et al., PCT No. 91/10444. Following treatment of rat testicular germ cells with activin, these cells were observed to proliferate 2.0–2.5 times faster than control cells. Additional studies have confirmed the initial description of activin's ability to stimulate FSH secretion from cultured rat pituitary cells by about 2–3 fold (Vale et al., *Nature* 321: 776–779 (1986); Ling et al., *Nature* 321: 779–782 (1986); Carroll et al., *Molecular Endocrinology*, 3:1969–1976 (1989); Kowaga et al., *Endocrinology* 128, 1682–1684 (1991); Attardi et al., *Mol. Endo.* 4: 721 (1990)). Although these results raise the possibility that activin may increase fertility in mammalian subjects, the measured increase in FSH secretion is typically small.

Recent results suggest that the importance of activin to maintenance of FSH biosynthesis is much greater than has previously been recognized. The mRNA for the $\beta$ subunits of FSH become rapidly undetectable in pituitary cells cultured in a way to remove endogenous-secreted activin (Weiss et al., *Endocrinology* 131: 1403–1408 (1992)). When activin is then added back to the medium, these low levels of FSH mRNA increase 30–70 fold, a substantially greater increase than the 2–3 fold stimulation that is observed when cells are cultured in the presence of endogenous activin.

The biological activity of FSH can be influenced by the presence of a binding protein, such as follistatin (FS) (Ling et al., *Nature* 321: 779–782 (1986)), which may form complexes with activin (Krummin et al., *Endocrinology* 132: 431 (1993)). Recent studies indicate that incubation of rat pituitary cultures with an immunoneutralizing antibody raised against activin results in a decline in FSH secretion (Corrigan et al. *Endocrinology*, 128:1682–1684 (1991)), and that FS acts similarly by binding to activin, thereby neutralizing its FSH-releasing activity (Kowaga et al., *Endocrinology* 128, 1682–1684 (1991)).

SUMMARY OF THE INVENTION

In general, the invention features a method for contraception by inhibiting the synthesis and/or release of FSH in a patient, the method featuring the step of administering to the patient a contraceptive agent having activin-antagonist activity such that the contraceptive agent results in inhibition of the activin-stimulated synthesis and/or release of FSH, resulting in a decrease in fertility and facilitating contraception in the patient.

In preferred embodiments of the invention, a peptide or non-peptide mimetic having activin-antagonist activity is used as the contraceptive agent. The amino acid sequence of the peptide or chemical structure of the non-peptide mimetic is sufficiently homologous with the receptor binding region of the human activin $\beta$ subunit such that it can effectively bind to the activin receptor sites and inhibit activin-stimulated release of FSH.

In a particular embodiment, the peptide contains between 8 and 70 amino acids, preferably a region at least 8 amino acids in length, and more preferably 15 amino acids in length, which is at least 80% homologous with a portion of the binding region of the activin $\beta$ subunit; preferably, the portion of the binding region includes the N-terminal or C-terminal 8 amino acids of the binding region.

In particular embodiments of the invention, the peptide contains an amino acid sequence selected from the group consisting of:

Val Pro Thr Lys Leu Arg Pro Met Ser Met Leu Tyr Tyr Asp Asp Gly Gln (SEQ. ID NO. 1) (amino acids 82–98 of the activin $\beta_A$ subunit) and Asn Ile Ile Lys Lys Asp Ile Gln Asn Met Ile Val Glu Glu Cys Gly (SEQ. ID NO. 2) (amino acids 99–114 of the activin $\beta_A$ subunit), or a substantially homologous variant thereof. In a preferred embodiment, the peptide includes an amino acid sequence substantially homologous to the sequence:

Val Pro Thr Lys Leu Arg Pro Met Ser Met Leu Tyr Tyr Asp Asp Gly Gln Asn Ile Ile Lys Lys Asp Ile Gln Asn Met Ile Val Glu Glu Cys Gly (SEQ ID NO. 3) (amino acids 82–114 of the activin $\beta_A$ subunit).

In another embodiment of the invention, the contraceptive agent includes a protein having activin-antagonist activity which is capable of binding to activin to inhibit activin-stimulated release of FSH. In a particular embodiment, the protein is FS or a protein substantially homologous to FS.

By "substantially homologous" is meant an amino acid sequence which differs from a region of the activin $\beta$ subunit only by conservative amino acid substitutions, for example, substitution of one amino acid for another of the same class (e.g., valine for glycine, arginine for lysine, etc.) or by one or more non-conservative substitutions, deletions, or insertions located at positions which do not destroy the binding function of the peptide, but confer greater stability and antagonist activity. Preferably, a peptide is greater than 80% homologous (i.e., greater than 80% identical) to a region of the activin β subunit.

In yet another preferred embodiment of the invention, the contraceptive agent features a modified activin receptor having activin-antagonist activity which is capable of both binding activin and inhibiting activin-induced signaling once activin is bound, resulting in inhibition of activin-stimulated release of FSH. Alternatively, the modified activin receptor can attach to an activin receptor to form a complex. The complex is capable of binding activin, and inhibits activin-induced signaling once activin is bound, resulting in inhibition of activin-stimulated release of FSH. In preferred embodiments, the complex is a dimer.

Other features and advantages of the invention will be apparent from the following detailed description, and from the claims.

DETAILED DESCRIPTION

Figure 1:
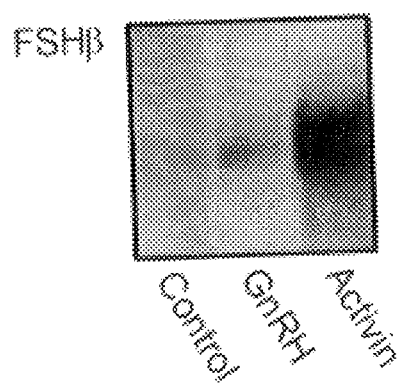
FIG. 1 is a contrast image showing the stimulation of FSH mRNA levels by activin or pulsatile GnRH in perifused pituitary cells.

The method of providing contraception by antagonizing the effects of activin was in part motivated by Applicants' discovery that activin is a more potent activator of FSH β subunit mRNA production than previously described. Using an assay involving the continuous infusion of activin in cultured pituitary cells, it was determined that activin increased levels of FSH mRNA production by 30–70 fold, a level more than an order of magnitude greater than that previously reported. In animals, FSH secretion results in stimulation of spermatogenesis in the testis and secretion of estradiol by the ovarian follicles, thus the inhibition of activin-stimulated FSH release is an effective method for contraception.

Activin-stimulated release of FSH can be inhibited by a number of different mechanisms. Hormone binding proteins which compete for binding to the activin receptor are shown to regulate the bioactivity of activin. Binding proteins which form complexes with activin may also effect the release of FSH. One example of such a protein is FS, which can bind directly to activin, thus reducing its bioactivity. The action of activin can also be regulated by modifying the receptor involved with binding. Receptors can be constructed so that the binding and membrane-spanning domains are the same as those of the normal activin receptor, but the intracellular sequences required for signalling are absent. In this case, the binding of activin to the receptor is uninhibited, but the activin-stimulated signalling of the receptor is effectively blocked.

There now follows a description of the effect of activin antagonists on the secretion of FSH, and the methods used to make such antagonists.

Regulation of FSH mRNA Levels by Activin in Perifusion Columns

The experiments described below used to investigate the regulation and secretion of FSH subunit mRNA levels by activin and GnRH are described in Weiss et al., *Endocrinology* 131: 1403–1408 (1992).

Pituitary cells were cultured using a perifusion column which allowed continuous infusion of activin and removal of endogenously secreted activin from the culture, resulting in activin-enhanced stimulation of FSH mRNA levels in perifused pituitary cells which is an order of magnitude greater than the response seen previously in static cell cultures (Kowaga et al., *Endocrinology* 128, 1682–1684 (1991); Attardi et al., *Mol. Endo.* 4: 721 (1990)). The effects of pituitary-derived factors are minimized by continuous perifusion, making it possible to assess the sensitivity of unstimulated cells to exogenously-administered activin. For example, the response of cells in static culture to activin may be preempted by the stimulatory effects of endogenously produced pituitary factors. These factors would be rapidly removed from perifusion columns but appear to accumulate in culture dishes and mask the effects of exogenous stimulation.

For the experiments described hereafter, cells were perifused with activin, cultured, and analyzed as described previously (Weiss et al., *Endocrinology* 131: 1403–1408 (1992); Weiss, et al., *Endocrinology* 127:2364–2371 (1990)).

Gonadotropin Subunit mRNA Levels After Activin Treatment

In an initial experiment, the response of FSH mRNA to recombinant activin was compared with the response to GnRH, a known hypophysiotropic stimulator of FSH mRNA levels (Gharib, et al., *Endocrine Reviews*, 11:177–199 (1990)). The comparison was made between pituitary cells processed in a perifusion column, allowing the dual advantage of continuously removing endogenously produced factors and allowing the administration of a pulsatile signal, which is critical for GnRH stimulation of FSH expression (Weiss, et al., *Molecular Endocrinology*, 4:557–564 (1990)). Cells were prepared for perifusion as described previously (Weiss, et al, *Mol. End.* 4:557–564, (1990)). Individual columns were perifused for 10 hrs with either perifusion medium (RPMI-1640 containing 2 g/l NaHCO$_3$, 0.25% BSA (Fraction V; Sigma, St. Louis, Mo.)) alone, hourly pulses of 10 nM GnRH, or a continuous infusion of a maximal concentration of activin (50 ng/ml). At the end of the experiment, total RNA was prepared and quantitated by a northern blot analysis described previously (Weiss, et al, *Mol. End.* 4:557–564, (1990)).

Referring now to FIG. 1, FSH levels were increased following exposure to GnRH and activin. In the experiment, GnRH was administered as hourly 5 min. pulses and activin was administered continuously over 10 hrs., while the control column received perifusion medium alone. Application of pulsatile GnRH elicited a 2.7-fold increase in the level of FSH mRNA compared to application of the perifusion medium alone. More striking was the response of FSH mRNA to activin in perifusion; the observed 55-fold increase in FSH mRNA levels was considerably larger than the previously reported effects of activin in plated cell cultures.

Figure 2:
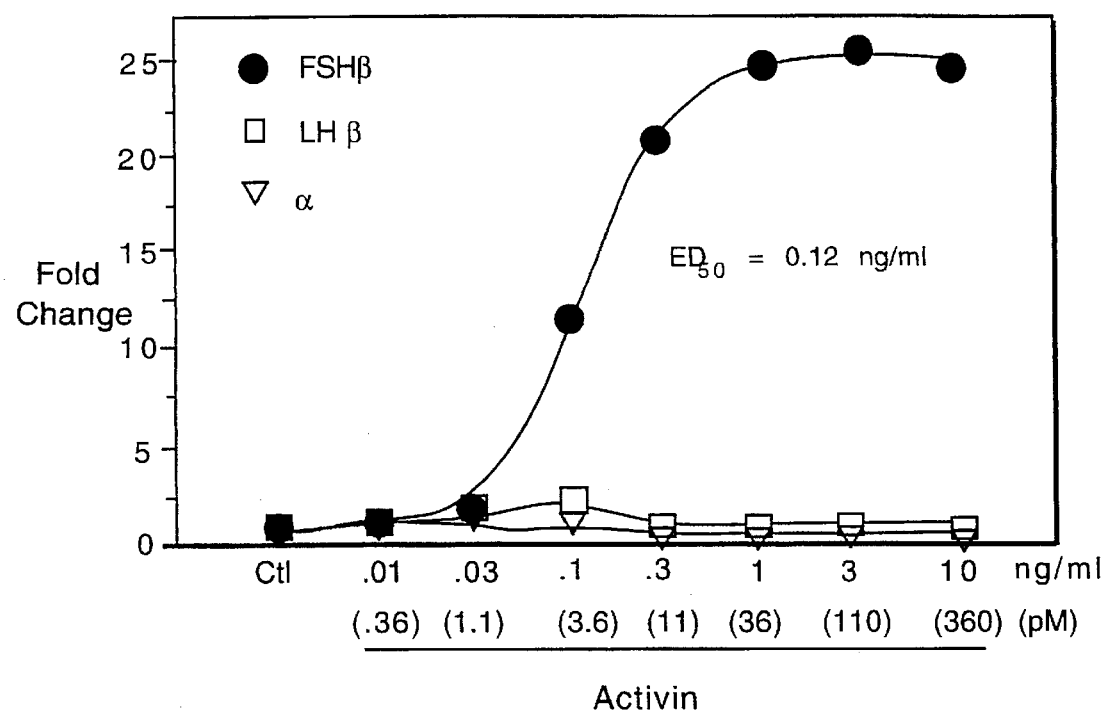
FIG. 2 is a plot showing gonadatropin subunit mRNA levels as a function of activin concentration in perifusion experiments.

The disparity in response between perifused cells and cells cultured in dishes was examined further using a range of activin concentrations. Referring now to FIG. 2, activin concentrations exceeding 0.03 ng/ml resulted in an increase in FSH levels during perifusion experiments. FSH subunit mRNA levels were calculated as a ratio to GAPDH, and were expressed in terms of fold change relative to columns receiving perifusion medium alone. Molar concentrations of activin were calculated from mass amounts assuming a molecular weight of 28000 g/mol. for recombinant activin. Results were confirmed using additional experiments involving perifusion medium alone and medium containing concentrations of activin ranging from 0.01 ng/ml to 10 ng/ml. In all cases, activin was exceptionally effective and highly specific for stimulation of FSH mRNA levels.

Referring again to FIG. 2, a detectable increase in the level of FSH mRNA was measured using 0.03 ng/ml of activin (1.79-fold, not clear on this scale), and stimulation exceeded 10-fold at 0.1 ng/ml, which approximates the $ED_{50}$ (0.12 ng/ml) for activin in this system. 25-fold stimulation was achieved at 1 ng/ml activin, with higher concentrations eliciting no additional response in this experiment. In additional experiments, elevations of FSH mRNA levels in response to higher concentrations of activin (3 ng/ml) ranged from 20-fold to greater than 75-fold.

For comparison, a concentration of activin (5 ng/ml) that maximized FSH levels in the perifusion system was tested in plated cell cultures. Cells were cultured for 3 days and then exposed to fresh medium with and without activin for 72 hours. In the experiment, mRNA levels were calculated and expressed as described for FIG. 2. Under these conditions, activin was considerably less effective in stimulating the release of FSH, eliciting only a 2.7-fold increase in the mRNA level.

Time-Course of FSH mRNA Expression After Pituitary Cell Dispersion

The continuous flow of fresh medium through perifusion columns removes secreted factors (released by the perifused cells) which normally accumulate in static culture dishes. To examine the possibility that endogenous factors were stimulating pituitary cells in plated cell cultures and thereby preventing the full response to exogenous activin, the dynamic changes in FSH mRNA levels from the time of pituitary dispersion were monitored in culture dishes during a 3-day period. Total RNA was extracted from equal cell aliquots immediately after dispersion at different times after being placed into culture dishes. Expression of FSH mRNA fell very rapidly after dispersion, declining to 8% of its original level at 4 hrs, and remained low (15% of the original level) 8 hrs after dispersion. The level of FSH mRNA increased to 68% of the original level 24 hrs after dispersion, and continued to rise, exceeding twice the immediate post-dispersion level by 3 days.

Interference of FSH Biosynthesis

Release of FSH from the anterior pituitary is essential for gametogenesis, and results in stimulation of spermatogenesis in the testis and secretion of estradiol by the ovarian follicles. Methods of antagonizing the activin-stimulated release of FSH in a patient are used in the present invention as a way of providing contraception.

In one method of the invention, FSH biosynthesis can be blocked using molecules which compete for the activin receptor, thus inhibiting activin-induced release of FSH. Alternatively, compounds which form complexes directly with activin, such as FS, can block activin's biological activity without actually competing for the activin receptor site. Another method of the present invention used for inhibiting activin-induced release of FSH involves using a modified activin receptor as the activin antagonist. It is possible to construct an activin receptor which lacks the intracellular sequences required for signaling, but has binding and membrane spanning domains capable of binding activin. In this case, activin binding is not affected, but activin signalling is inhibited, resulting in a decrease in activin-induced FSH biosynthesis.

The methods of contraception of the present invention using activin antagonists are carried out as follows.

Example 1—FS as an Activin Antagonist

Figure 3:
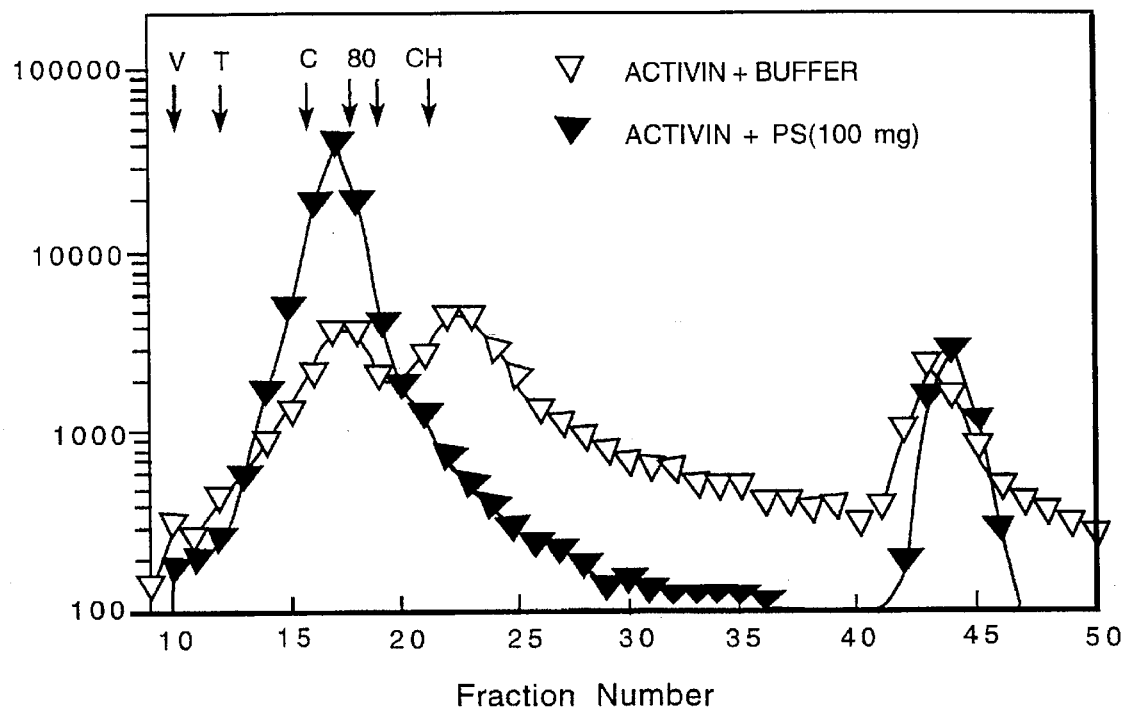
FIG. 3 is a plot showing the molecular weight shift in activin-FS compounds compared to unbound activin in buffer.

Inhibition of activin's biological activity through binding with FS was monitored with the following experiments. Radiolabelled activin was incubated with serum samples and chromatographed on a gel filtration column, resulting in two peaks corresponding to FS-activin complexes. Each peak corresponded to a higher apparent molecular weight than the peaks observed for activin chromatographed in buffer alone. Referring now to FIG. 3, 100 ng FS bound all of the radiolabelled activin, resulting in a sharp peak eluting with $M_r$ 120–150 which was narrow and of greater intensity than the peak observed for the FS-activin complex in serum. When radiolabelled inhibin was incubated with a similar concentration of FS as used for activin, a shift of radioactivity to higher $M_r$ was observed, but not in the form of a sharp peak as observed for activin. The broad peak elutes at an $M_r$ of approximately 65–200,000, amounting to only a small amount of the radiolabelled inhibin added, suggesting the affinity of FS is much lower for inhibin than for activin.

Figure 4:
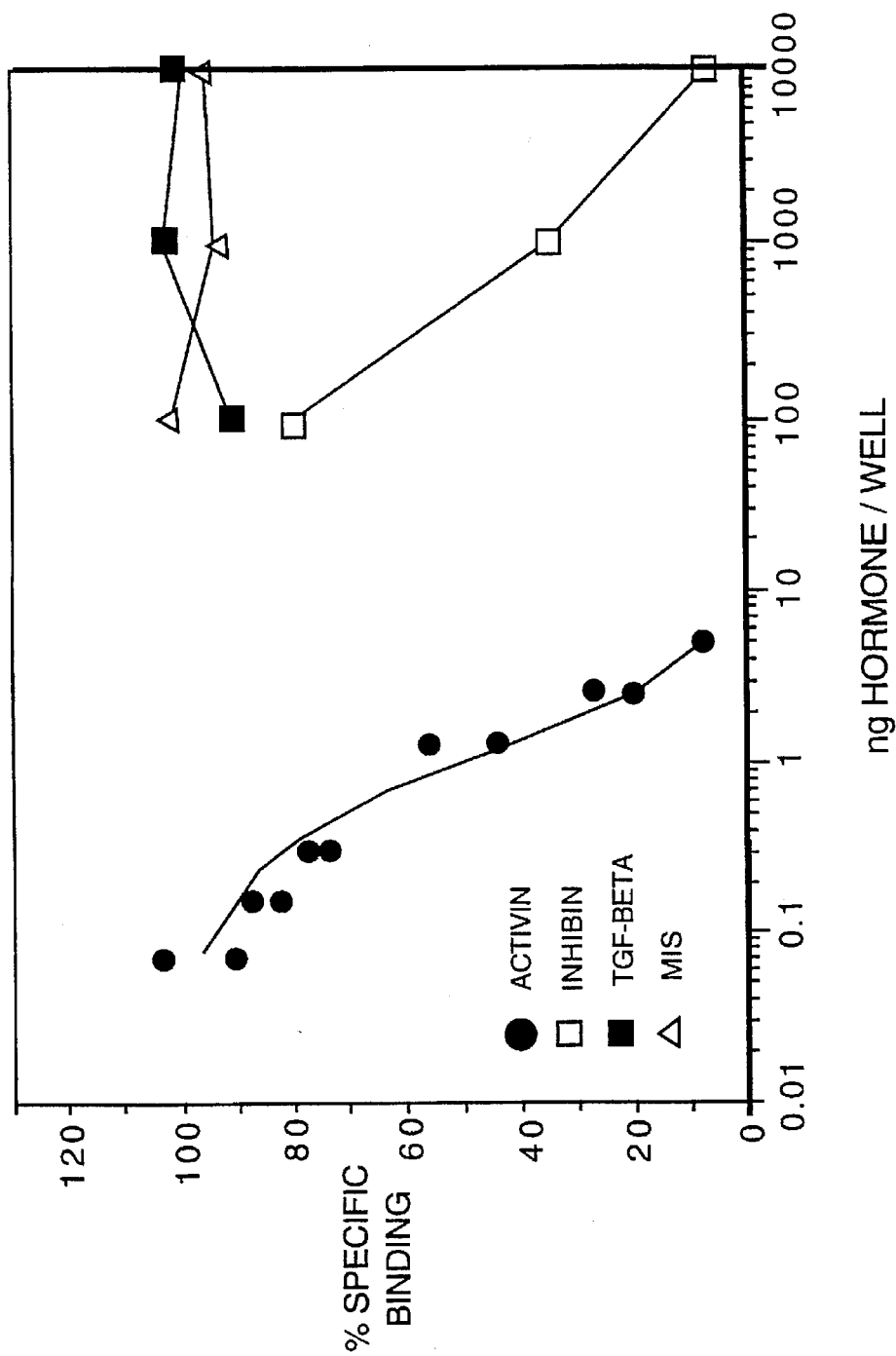
FIG. 4 is a plot showing the specific binding of activin and inhibin as a function of FS concentration.

Selectivity of FS recognition of activin was determined with the solid phase assay described herein. In the assay, the maximal binding of radiolabelled activin was observed to be 50%, and was obtained with 25–50 ng FS adsorbed to the plates. This insures that a majority of FS binding sites would be occupied by added trace compounds. This increases the likelihood that competition, if present, would be detected. Referring to FIG. 4, unlabelled FS inhibits binding of radiolabelled activin with an $ED_{50}$ of approximately 1 ng. A similar inhibition curve with unlabelled inhibin was parallel to that of activin, although the binding was inhibited with an $ED_{50}$ of approximately 500 ng, suggesting a 500-fold decrease in relative potency. In contrast, the related hormones TGF-β and MIS did not bind to FS at doses comparable to those used for inhibin. These results demonstrate that FS is selective in its recognition of inhibin and activin through the common $β_A$ subunit, with activin being greatly preferred, and that both activin and inhibin form complexes with FS.

Figure 5:
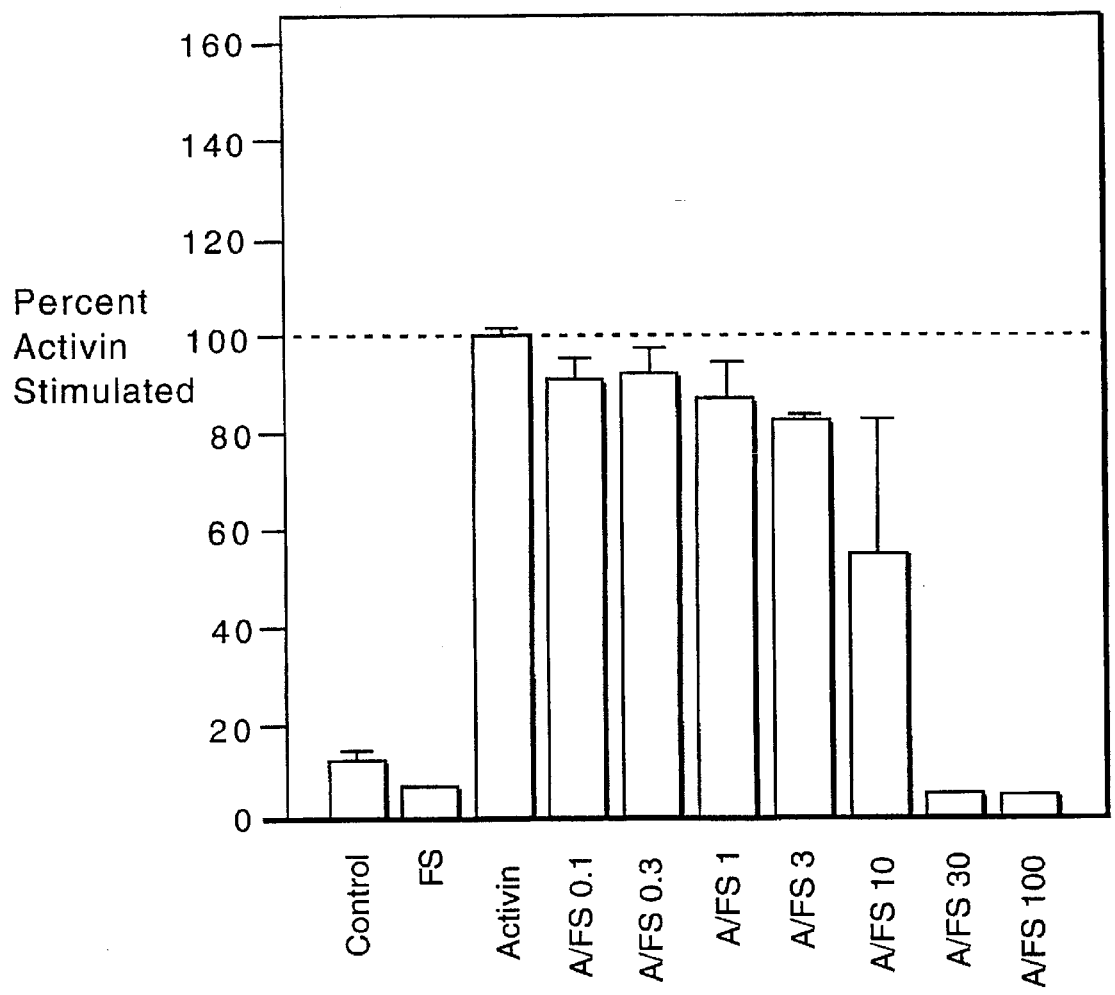
FIG. 5 is a plot showing the percentage of activin stimulated as a function of FS concentration.
Figure 7:
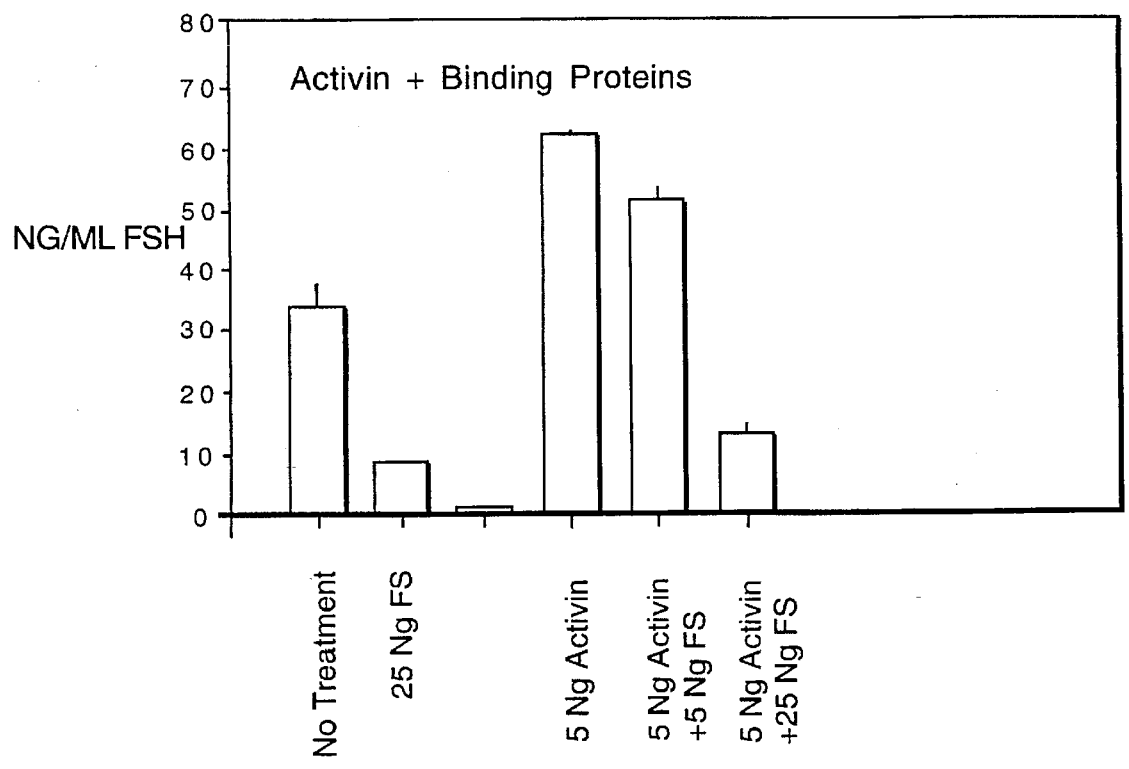
FIG. 7 is a plot showing the dependence of FSH release on activin, FS, and activin-FS complexes.

FS-activin complexes inhibit the biological activity of activin, and reduce activin-stimulated release of FSH. Referring now to FIGS. 5 and 7, pituitary cells were cultured using a perifusion column, which allowed continuous infusion of activin and removal of endogenously secreted activin from the culture, and then treated with activin and FS. As seen from the graphs, FS can concentration-dependently block activin stimulation, eventually resulting in the inhibition of FSH biosynthesis. The perifusion system described previously was used to expose cells to activin or FS alone or combined. When administered alongside of activin, a FS concentration of 10 ng/ml inhibits activin stimulation by approximately 60% (FIG. 5). Increasing the FS concentration to 30 ng/ml in the same experiment lowers the amount of activin stimulated to less than 10% of the level induced in the absence of FS, while higher concentrations appear to have no additional effect. These results indicate the ability of FS to inhibit the biological activity of activin, and thus block activin-stimulated release of FSH.

Example 2—Synthetic Peptides as Activin Antagonists

FSH biosynthesis can also be inhibited with molecules designed to compete with activin for the activin receptor, resulting in inhibition of activin-stimulated release of FSH.

In order to design a molecule capable of competing for the activin receptor region, the binding between FS and activin (determined by the experiments described in Example 1) was used to determine a region of the activin molecule having biological activity. Substantially pure FS was characterized in human serum using gel filtration, chromatography, SDS-PAGE/Western blotting techniques, and kinetic analysis. Compounds featuring FS bound to radiolabeled and unlabeled activin were analyzed using a gel filtration apparatus by observing shifts in molecular weight of labeled activin when bound to FS. Overlapping synthetic peptides were used to determine two primary domains in the FS-activin binding region, one near the N-terminus and the other near the C-terminus.

Peptides used to map the activin binding region were synthesized using techniques described previously (Grausepohl et al., *Peptide Chemistry, Structure and Biology*, Rivers and Marshall, eds., p. 102, (1990)). Overlapping 15-mer peptides spanning the entire inhibin/activin $\beta_A$ subunit were synthesized on an Abimed 422 automated synthesizer as amides, except for the C-terminal peptide, which was a free acid. The purity of each peptide was accessed by HPLC, and confirmation that the major component of each peptide was the desired sequence was obtained by mass spectrometry.

Figure 6:
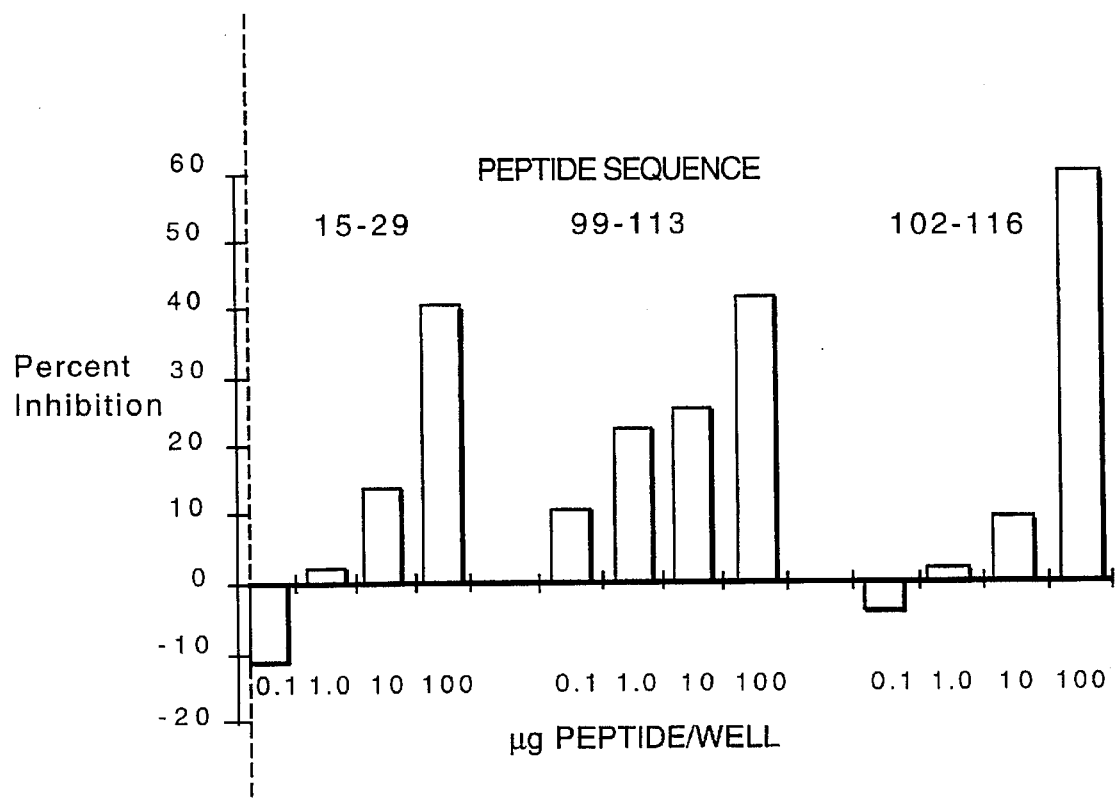
FIG. 6 is a plot showing the inhibition of activin's interaction with FS by several synthetic peptides due to overlap with FS-activin binding region.

To be considered active, a peptide had to demonstrate dose-dependent inhibition of activin-FS binding in at least three assays. Referring now to FIG. 6, three 15-mer synthetic peptides demonstrated consistent inhibition, with the degree of inhibition increasing with increasing concentration of the peptide. Two of the peptides overlap, indicating that the activin binding region contains a minimum of two primary domains, one contained within the N-terminus (amino acid sequence 15–29 of the activin $\beta_A$ subunit: Gln Phe Phe Val Ser Phe Lys Asp Ile Gly Trp Asn Asp Trp Ile (SEQ ID NO. 4)) and the other domain near the C-terminus (amino acid sequence 102–113 of the activin $\beta_A$ subunit: Lys Lys Asp Ile Gln Asn Met Ile Val Glu Glu Cys (SEQ ID NO. 5)).

Due to similar homology, the recently published crystal structure of TGF-$\beta$ was used as a likely model for activin. The structure of this compound indicates that the domains are located at opposite ends of the folded activin molecule. As suggested by the crystal structure, the 102–113 sequence of one subunit is juxtaposed to the N-terminus of the disulfide-linked subunit including the 15–29 sequence.

Synthetic peptides were manufactured as described above and then tested for the ability to inhibit activin's action at the pituitary by binding to the activin receptor, thus blocking FSH release. The amino acid sequence of the BIN-3 (SEQ ID NO. 3) peptide was composed of the amino acid sequence 82–114 of the activin $\beta_A$ subunit, derived from the binding region near the C-terminal end of the activin molecule. Other amino acid sequences taken from this region, such as 82–98 (BIN-4; SEQ. ID NO. 1) 99–114 (BIN-2; SEQ. ID NO. 2), and 66–80 (BIN-1) were also tested as activin antagonists. Other antagonist candidates can be routinely screened using this assay.

Initial column chromatography experiments eluting labeled BIN-3 (SEQ. ID NO. 3) with serum and buffer solutions show evidence for the formation of an FS-BIN-3 complex, indicating that the BIN-3 (SEQ. ID NO. 3) amino acid sequence is representative of the activin binding region, and may function as an activin antagonist.

Figure 8:
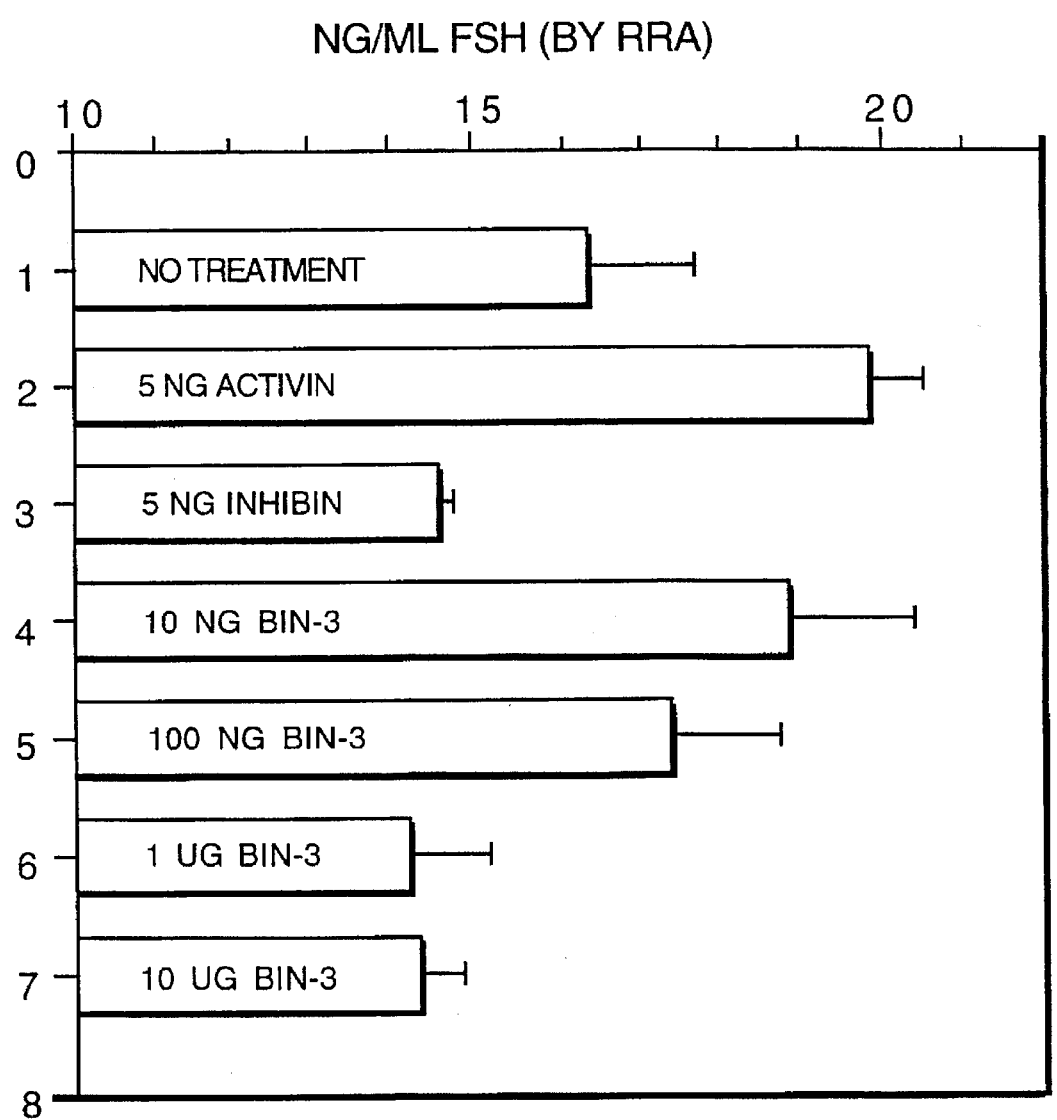
FIG. 8 is a plot showing the dependence of FSH release on the synthetic peptide BIN-3 (SEQ ID NO. 3).
Figure 9:
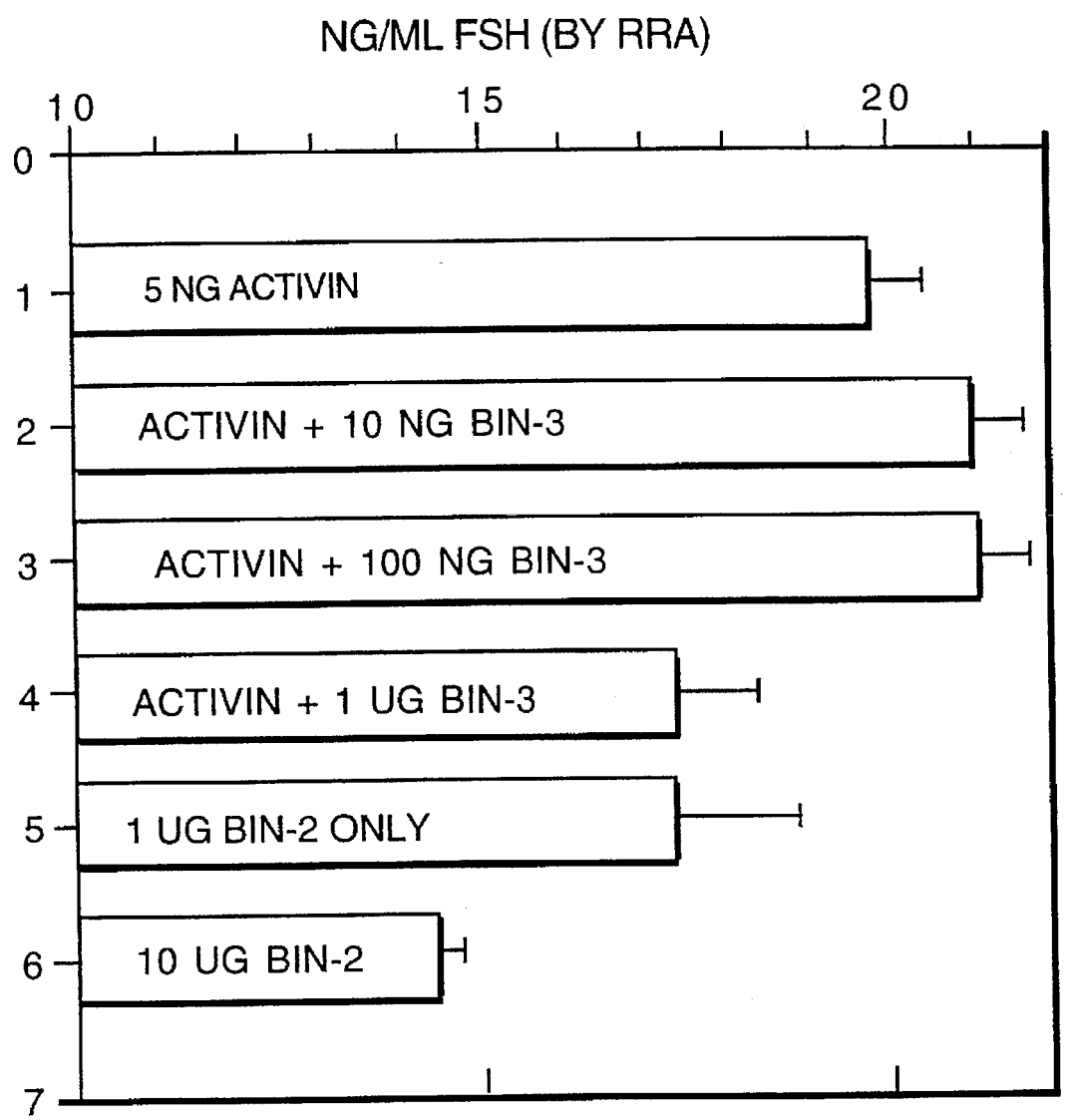
FIG. 9 is a plot showing the dependence of FSH release on BIN-2 (SEQ. ID NO. 2) and BIN-3 (SEQ. ID NO. 3) in the presence of activin.

Referring now to FIGS. 8 and 9, BIN-3 (SEQ. ID NO. 3) inhibits basal and activin-stimulated FSH secretion when applied to static, plated cultures of rat pituitary cells. Within experimental error, low doses (10–100 ng) of BIN-3 have no effect on the level of FSH. When higher doses (1–10 µg) of BIN-3 are applied to the cell cultures, the FSH level is lowered, with the decrease being about 12% relative to untreated cells, and about 27% relative to cells treated with 5 ng activin. Similarly, BIN-2 (SEQ ID NO. 2) lowers the basal FSH level by about 11% in the same assay when applied in 10 µg doses (FIG. 9). When added along with 5 ng activin to cells, a 1 µg dose of BIN-3 (SEQ. ID NO. 3) resulted in about a 12% decline in FSH level when compared to cells treated with activin alone, indicating the ability of BIN-3 (SEQ ID NO. 3) to act as an activin antagonist.

Alternatively, non-peptide mimetics having chemical structures sufficiently homologous with the receptor binding region of the human activin $\beta$ subunit can function as activin antagonists. These molecules are capable of binding to the activin receptor sites and inhibiting activin-stimulated release of FSH.

Example 3—Inhibin as an Activin Antagonist

Inhibin can concentration-dependently block activin simulation of FSH mRNA levels, partly due to competition by inhibin for binding to the activin receptor.

In order to monitor the inhibitory effects of inhibin, pituitaries from adult male Sprague-Dawley rats were dispersed and cells were perifused as described in Example 1. Cells were allowed to adhere to acrylamide beads loaded into perifusion columns and were perifused at a rate of 325 µl/min. with RPMI-1640 containing 2 g/liter NaHCO3, 0.25% BSA, and varying concentrations of activin and inhibin. Measurements of FSH$\beta$ MRNA were calculated as ratios to GAPDH MRNA.

Using the in vitro perifusion system, equal mass amounts (3 ng/ml) of activin and inhibin resulted in a 72% decrease in FSH$\beta$ mRNA levels compared to levels induced by activin stimulation alone. A maximal concentration of inhibin (30 ng/ml) suppressed FSH$\beta$ mRNA levels by 83%. A 10-fold excess of inhibin was necessary to attenuate the effects of activin entirely.

Whole cell receptor assays using $^{125}$I-labeled activin confirmed that the inhibin used in the perifusion experiments competed for activin binding sites, although with lower affinity. Direct competition at the activin receptor therefore accounts for part of the activin/inhibin antagonism observed at the level of FSH mRNA.

Example 4—Inhibition of Activin Signalling by a Modified Activin Receptor

In another aspect of the invention, the activin receptor can be mutated so that it is capable of binding activin, but incapable of signaling once activin is bound. Disrupting the activin signal pathway represents another mechanism in which activin action can be blocked, and activin-induced FSH biosynthesis can be inhibited. Receptors mutated as such might also block the function of normal, wild type activin receptors if they are capable of dimerization. This dominant negative mechanism has been demonstrated in principle for activin receptors.

Activins have been shown previously to induce mesoderm in embryonic explants (Symes et al., *Development* 101: 185–408 (1967)). Using analogy with signal transduction by tyrosine kinase receptors, e.g., the receptor for fibroblast growth factor (bFGF), experiments which indicate that a truncated activin receptor will interfere with the function of endogenous activin receptor by creating an inactive receptor heterodimer were carried out by Hemmati-Brivanlou et al., *Nature*, 359: 609–614 (1992), the results of which are incorporated herein by reference.

Truncated activin receptors were constructed using a fragment of DNA from a wild-type receptor encoding the entire extracytoplasmic domain (including the signal sequence), the transmembrane domain, and 10 amino acids from the cytoplasmic domain (excluding the serine/threonine kinase domain). The DNA were entirely free of 5' and 3' untranslated sequences, and were subcloned in pSP64T cells (Kreig et al., *Nucleic Acids Res.* 12, 7057–7070 (1984)). Synthetic RNA encoding the truncated activin receptor were injected into the animal pole of two-cell embryos from female *Xenopus laevis,* and the effects on isolated animal caps were qualitatively assessed by the presence or absence of tissue-specific molecular markers. These data indicate that the truncated receptor completely and specifically blocks the early morphogenetic response of animal caps exposed to activin. Early and late molecular markers for mesoderm induction are also specifically blocked by the truncated activin receptor. In addition, expression of muscle actin, a mesoderm-specific gene that is expressed at the end of gastrulation, is also selectively inhibited in animal caps injected with the truncated receptor.

Experimental results also indicate that bFGF induces muscle actin to roughly 10-fold higher levels in animal caps injected with the truncated activin receptor compared with control caps. These data show that activin antagonizes the mesoderm-inducing capacity of bFGF, and that the mutant receptor can effectively inhibit the effects of activin. Thus, by altering the activin receptor so that binding occurs but signalling is inhibited, the action of activin is selectively blocked.

Methods of Use

The activin antagonists of the invention can be administered to a sexually-mature mammal, particularly a human, via one of the traditional modes (e.g., orally, parenterally, transdermally, or transmucosally), in a sustained-release formulation using a biodegradable, biocompatable polymer, or by on-site delivery using micelles, gels and liposomes. If injected, the peptides of the invention are mixed with a balanced salt solution at pH 7.4–7.5, e.g., 1X phosphate buffered saline at pH 7.4.

Dosages of the antagonists will vary, depending on factors such as half-life of the substance, potency, route of administration, and the condition of the patient. Generally, in order to act as an effective contraceptive agent, the antagonist should be administered to the patient in a dosage of about 10 to 250 µg/kg/day, preferably 50 to 100 µg/kg/day.

The foregoing descriptions of preferred embodiments of the invention have been presented for purposes of illustration and description. They are not intended to be exhaustive or to limit the invention to the precise form disclosed. The embodiments chosen are described in order to best explain the principles of the invention.

What is claimed is:

1. A method for contraception by inhibiting release, biosynthesis, or release and biosynthesis of FSH in a human patient, said method comprising:

administering to said patient a contraceptive agent comprising a peptide having activin-antagonist activity, said peptide being between 2 and 70 amino acids in length and comprising an amino acid sequence which is sufficiently homologous with a receptor binding region of human activin β subunit so that said peptide, once administered, complexes with the activin receptor such that said contraceptive agent inhibits activin-stimulated release, biosynthesis, or release and biosynthesis of FSH, thereby resulting in a decrease in fertility and facilitating contraception in said patient.

2. A method for contraception by inhibiting release, biosynthesis, or release and biosynthesis of FSH in a human patient, said method comprising:

administering to said patient a contraceptive agent comprising a peptide having activin-antagonist activity, said peptide being between 2 and 70 amino acids in length and comprising an amino acid sequence which complexes with activin following administration to inhibit activin-stimulated release, biosynthesis, or release and biosynthesis of FSH, thereby resulting in a decrease in fertility in said patient.

3. A method for contraception by inhibiting release, biosynthesis, or release and biosynthesis of FSH in a human patient, said method comprising:

administering to said patient a contraceptive agent comprising a modified activin receptor having activin-antagonist activity, said modified activin receptor, following administration, complexing with an activin receptor to form a complex capable of complexing activin and inhibiting activin-induced signaling once activin is bound, said contraceptive agent inhibiting activin-stimulated release, biosynthesis, or release and biosynthesis of FSH, thereby resulting in a decrease in fertility in said patient.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Val Pro Thr Lys Leu Arg Pro Met Ser Met Leu Tyr Tyr Asp Asp Gly
 1               5                  10                      15
Gln
```

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Asn  Ile  Ile  Lys  Lys  Asp  Ile  Gln  Asn  Met  Ile  Val  Glu  Glu  Cys  Gly
1              5                        10                       15
```

( 2 ) INFORMATION FOR SEQ ID NO:3:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Val  Pro  Thr  Lys  Leu  Arg  Pro  Met  Ser  Met  Leu  Tyr  Tyr  Asp  Asp  Gly
1              5                        10                       15

Gln  Asn  Ile  Ile  Lys  Lys  Asp  Ile  Gln  Asn  Met  Ile  Val  Glu  Glu  Cys
               20                       25                       30

Gly
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Gln  Phe  Phe  Val  Ser  Phe  Lys  Asp  Ile  Gly  Trp  Asn  Asp  Trp  Ile
1              5                        10                       15
```

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Lys  Lys  Asp  Ile  Gln  Asn  Met  Ile  Val  Glu  Glu  Cys
1              5                        10
```